United States Patent [19]
Galli et al.

[11] Patent Number: 5,869,298
[45] Date of Patent: Feb. 9, 1999

[54] STABLE MUTANTS OF D-N-α-CARBAMOYLASE AND PROCESS FOR PREPARING D-α-AMINO ACIDS

[75] Inventors: Giuliano Galli, San Donato Mil.se; Renata Grifantini, Milan; Guido Grandi, Segrate San Felice, all of Italy

[73] Assignee: Eniricerche S.p.A., S.Donato Mil.se, Italy

[21] Appl. No.: 415,343

[22] Filed: Apr. 3, 1995

[30] Foreign Application Priority Data

Apr. 15, 1994 [IT] Italy .................................. MI94A0725

[51] Int. Cl.⁶ .......................... C12P 13/04; C12P 19/56; C12N 9/14
[52] U.S. Cl. ............................. 435/106; 435/78; 435/195
[58] Field of Search ............................. 530/350; 435/7.6, 435/106, 78, 195

[56] References Cited

FOREIGN PATENT DOCUMENTS

| 0 281 822 | 9/1988 | European Pat. Off. . |
|---|---|---|
| 0515698 | 12/1992 | European Pat. Off. . |
| 0 610 517 | 8/1994 | European Pat. Off. . |
| 0677585 | 10/1995 | European Pat. Off. . |
| WO 94/00577 | 1/1994 | WIPO . |

OTHER PUBLICATIONS

Buson et al. 1996 FEMS Microbiol. Lett 145:55–62.
Grifantini et al 1996 J. Biol. Chem. 271:9326–9331.
Ogawa et al 1994 J Biotech 38:11–19, p. 11 only.
Kim et al 1995 Enz & Microbiol Technol 17:63–67 p. 63 only.

*Primary Examiner*—Karen C. Carlson
*Attorney, Agent, or Firm*—Oblon, Spivak, McClelland, Maier & Neustadt, P.C.

[57] ABSTRACT

The present invention relates to mutants of D-N-α-carbamylase wherein at least one of the cysteines in position 243, 250 and 279 of the amino acid sequence of the wild type enzyme is substituted with a different residue selected from natural amino acids; a recombinant plasmid comprising a nucleotidic sequence which encodes for at least one of the mutants of D-N-α-carbamylase, host microorganisms transformed with said plasmid and a process for the preparation of these mutants by the culture of said microorganisms. The mutants of D-N-α-carbamylase have a higher enzymatic stability than that of the wild type enzyme and are particularly useful in the preparation of D-α-amino acids providing an improvement in the production yields.

6 Claims, 2 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:1:

GAGCAGCATG GCCCCCTCCT CC      22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCCACGATG GCCGAATGGC C      21

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCAGTTCCCG GGCGCGGTCG AGAT                                                24
```

( 2 ) INFORMATION FOR SEQ ID NO:4:

( i ) SEQUENCE CHARACTERISTICS:
        ( A ) LENGTH: 915 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ATG ACA CGT CAG ATG ATA CTT GCT GTC GGA CAG CAA GGC CCC ATC GCG          48
Met Thr Arg Gln Met Ile Leu Ala Val Gly Gln Gln Gly Pro Ile Ala
 1               5                  10                  15

CGA GCG GAG ACA CGC GAA CAG GTG GTT GGC CGC CTC CTC GAC ATG TTG          96
Arg Ala Glu Thr Arg Glu Gln Val Val Gly Arg Leu Leu Asp Met Leu
                 20                  25                  30

ACG AAC GCA GCC AGC CGG GGC GTG AAC TTC ATC GTC TTT CCC GAG CTT         144
Thr Asn Ala Ala Ser Arg Gly Val Asn Phe Ile Val Phe Pro Glu Leu
             35                  40                  45

GCG CTC ACG ACC TTC TTC CCG CGC TGG CAT TTC ACC GAC GAG GCC GAG         192
Ala Leu Thr Thr Phe Phe Pro Arg Trp His Phe Thr Asp Glu Ala Glu
         50                  55                  60

CTC GAT AGC TTC TAT GAG ACC GAA ATG CCC GGC CCG GTG GTC CGT CCA         240
Leu Asp Ser Phe Tyr Glu Thr Glu Met Pro Gly Pro Val Val Arg Pro
 65                  70                  75                  80

CTC TTT GAG ACG GCC GCC GAA CTC GGG ATC GGC TTC AAT CTG GGC TAC         288
Leu Phe Glu Thr Ala Ala Glu Leu Gly Ile Gly Phe Asn Leu Gly Tyr
                 85                  90                  95

GCC GAA CTC GTC GTC GAA GGC GGC GTC AAG CGT CGC TTC AAC ACG TCC         336
Ala Glu Leu Val Val Glu Gly Gly Val Lys Arg Arg Phe Asn Thr Ser
             100                 105                 110

ATT CTG GTG GAT AAG TCA GGC AAG ATC GTC GGC AAG TAT CGT AAG ATC         384
Ile Leu Val Asp Lys Ser Gly Lys Ile Val Gly Lys Tyr Arg Lys Ile
         115                 120                 125

CAT TTG CCG GGT CAC AAG GAG TAC GAG GCC TAC CGG CCG TTC CAG CAT         432
His Leu Pro Gly His Lys Glu Tyr Glu Ala Tyr Arg Pro Phe Gln His
 130                 135                 140

CTT GAA AAG CGT TAT TTC GAG CCG GGC GAT CTC GGC TTC CCG GTC TAT         480
Leu Glu Lys Arg Tyr Phe Glu Pro Gly Asp Leu Gly Phe Pro Val Tyr
145                 150                 155                 160

GAC GTC GAC GCC GCG AAA ATG GGG ATG TTC ATC TGC AAC GAT CGC CGC         528
Asp Val Asp Ala Ala Lys Met Gly Met Phe Ile Cys Asn Asp Arg Arg
                 165                 170                 175

TGG CCT GAA ACG TGG CGG GTG ATG GGA CTT AAG GGC GCC GAG ATC ATC         576
Trp Pro Glu Thr Trp Arg Val Met Gly Leu Lys Gly Ala Glu Ile Ile
             180                 185                 190

TGC GGC GGC TAC AAC ACG CCG ACC CAC AAT CCC CCC GTT CCC CAG CAC         624
Cys Gly Gly Tyr Asn Thr Pro Thr His Asn Pro Pro Val Pro Gln His
         195                 200                 205
```

| | | | | | | | | | | | | | | | | |
|---|---|---|---|---|---|---|---|---|---|---|---|---|---|---|---|---|
| GAC | CAT | CTG | ACG | TCC | TTC | CAC | CAC | CTT | CTG | TCG | ATG | CAG | GCC | GGG | TCG | 672 |
| Asp | His | Leu | Thr | Ser | Phe | His | His | Leu | Leu | Ser | Met | Gln | Ala | Gly | Ser | |
| | 210 | | | | | 215 | | | | | 220 | | | | | |
| TAC | CAA | AAC | GGC | GCC | TGG | TCC | GCG | GCG | GCC | GGC | AAG | GTC | GGC | ATG | GAG | 720 |
| Tyr | Gln | Asn | Gly | Ala | Trp | Ser | Ala | Ala | Ala | Gly | Lys | Val | Gly | Met | Glu | |
| 225 | | | | | 230 | | | | | 235 | | | | | 240 | |
| GAG | GGG | TGC | ATG | CTG | CTC | GGC | CAT | TCG | TGC | ATC | GTG | GCG | CCG | ACC | GGC | 768 |
| Glu | Gly | Cys | Met | Leu | Leu | Gly | His | Ser | Cys | Ile | Val | Ala | Pro | Thr | Gly | |
| | | | | 245 | | | | | 250 | | | | | 255 | | |
| GAA | ATC | GTT | GCC | CTG | ACC | ACG | ACG | TTG | GAA | GAC | GAG | GTG | ATC | ACC | GCC | 816 |
| Glu | Ile | Val | Ala | Leu | Thr | Thr | Thr | Leu | Glu | Asp | Glu | Val | Ile | Thr | Ala | |
| | | | 260 | | | | | 265 | | | | | 270 | | | |
| GCC | GTC | GAT | CTC | GAC | CGC | TGC | CGG | GAA | CTG | CGC | GAA | CAC | ATC | TTC | AAT | 864 |
| Ala | Val | Asp | Leu | Asp | Arg | Cys | Arg | Glu | Leu | Arg | Glu | His | Ile | Phe | Asn | |
| | | 275 | | | | | 280 | | | | | 285 | | | | |
| TTC | AAA | GCC | CAT | CGT | CAG | CCA | CAG | CAC | TAC | GGT | CTG | ATC | GCG | GAA | TTT | 912 |
| Phe | Lys | Ala | His | Arg | Gln | Pro | Gln | His | Tyr | Gly | Leu | Ile | Ala | Glu | Phe | |
| | 290 | | | | | 295 | | | | | 300 | | | | | |
| TGA | 915 | | | | | | | | | | | | | | | |

( 2 ) INFORMATION FOR SEQ ID NO:5:

( i ) SEQUENCE CHARACTERISTICS:
        ( A ) LENGTH: 304 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Thr | Arg | Gln | Met | Ile | Leu | Ala | Val | Gly | Gln | Gln | Gly | Pro | Ile | Ala |
| 1 | | | | 5 | | | | | 10 | | | | | 15 | |
| Arg | Ala | Glu | Thr | Arg | Glu | Gln | Val | Val | Gly | Arg | Leu | Leu | Asp | Met | Leu |
| | | | 20 | | | | | 25 | | | | | 30 | | |
| Thr | Asn | Ala | Ala | Ser | Arg | Gly | Val | Asn | Phe | Ile | Val | Phe | Pro | Glu | Leu |
| | | | 35 | | | | 40 | | | | | 45 | | | |
| Ala | Leu | Thr | Thr | Phe | Phe | Pro | Arg | Trp | His | Phe | Thr | Asp | Glu | Ala | Glu |
| | 50 | | | | | 55 | | | | | 60 | | | | |
| Leu | Asp | Ser | Phe | Tyr | Glu | Thr | Glu | Met | Pro | Gly | Pro | Val | Val | Arg | Pro |
| 65 | | | | | 70 | | | | | 75 | | | | | 80 |
| Leu | Phe | Glu | Thr | Ala | Ala | Glu | Leu | Gly | Ile | Gly | Phe | Asn | Leu | Gly | Tyr |
| | | | | 85 | | | | | 90 | | | | | 95 | |
| Ala | Glu | Leu | Val | Val | Glu | Gly | Gly | Val | Lys | Arg | Arg | Phe | Asn | Thr | Ser |
| | | | | 100 | | | | | 105 | | | | | 110 | |
| Ile | Leu | Val | Asp | Lys | Ser | Gly | Lys | Ile | Val | Gly | Lys | Tyr | Arg | Lys | Ile |
| | | | 115 | | | | | 120 | | | | | 125 | | |
| His | Leu | Pro | Gly | His | Lys | Glu | Tyr | Glu | Ala | Tyr | Arg | Pro | Phe | Gln | His |
| | | 130 | | | | | 135 | | | | | 140 | | | |
| Leu | Glu | Lys | Arg | Tyr | Phe | Glu | Pro | Gly | Asp | Leu | Gly | Phe | Pro | Val | Tyr |
| 145 | | | | | 150 | | | | | 155 | | | | | 160 |
| Asp | Val | Asp | Ala | Ala | Lys | Met | Gly | Met | Phe | Ile | Cys | Asn | Asp | Arg | Arg |
| | | | | 165 | | | | | 170 | | | | | 175 | |
| Trp | Pro | Glu | Thr | Trp | Arg | Val | Met | Gly | Leu | Lys | Gly | Ala | Glu | Ile | Ile |
| | | | 180 | | | | | 185 | | | | | 190 | | |
| Cys | Gly | Gly | Tyr | Asn | Thr | Pro | Thr | His | Asn | Pro | Pro | Val | Pro | Gln | His |
| | | | 195 | | | | 200 | | | | | 205 | | | |
| Asp | His | Leu | Thr | Ser | Phe | His | His | Leu | Leu | Ser | Met | Gln | Ala | Gly | Ser |
| | | | 210 | | | | 215 | | | | | 220 | | | |

| | | | | | | | | | | | | | | | |
|---|---|---|---|---|---|---|---|---|---|---|---|---|---|---|---|
| Tyr 225 | Gln | Asn | Gly | Ala | Trp 230 | Ser | Ala | Ala | Ala | Gly 235 | Lys | Val | Gly | Met | Glu 240 |
| Glu | Gly | Cys | Met | Leu 245 | Leu | Gly | His | Ser | Cys 250 | Ile | Val | Ala | Pro | Thr 255 | Gly |
| Glu | Ile | Val | Ala 260 | Leu | Thr | Thr | Thr | Leu 265 | Glu | Asp | Glu | Val | Ile 270 | Thr | Ala |
| Ala | Val | Asp 275 | Leu | Asp | Arg | Cys | Arg 280 | Glu | Leu | Arg | Glu | His 285 | Ile | Phe | Asn |
| Phe | Lys 290 | Ala | His | Arg | Gln | Pro 295 | Gln | His | Tyr | Gly | Leu 300 | Ile | Ala | Glu | Phe |

STABLE MUTANTS OF D-N-α-CARBAMOYLASE AND PROCESS FOR PREPARING D-α-AMINO ACIDS

The present invention relates to mutants of D-N-α-carbamoylase which have an improved enzymatic stability with respect to that of the wild type enzyme, means and methods for their preparation and their use for the preparation of D-α-amino acids.

The limitations in the industrial use of enzymes is generally due not only to their high production and purification costs, but also to their instability which, as is known, can be attributed to a series of factors such as for example thermal denaturation, oxidative phenomena and aggregations caused by bonds of the hydrophobic and/or covalent type.

Establishing the causes of instability of an enzyme is therefore of utmost importance in finding solutions for improving an enzymatic process and making it more competitive. On the other hand it is often difficult to exactly indicate (i) the causes of this instability and (ii) possible remedies for eliminating or reducing the instability without altering the activity of the enzyme.

D-N-α-carbamoylase is an enzyme which is capable of converting D-N-carbamyl-α-amino acids by means of stereoselective hydrolysis into the corresponding D-α-amino acids. These optically active compounds are important intermediates in the synthesis of pharmaco-logically active substances (for example, D-phenylglycine and D-para-hydroxyphenylglycine are used in the synthesis of penicillins and cephalosporins), pesticides (D-valine for the synthesis of the insecticide fluvanilate) or sweeteners (D-alanine).

D-N-α-carbamoylase is also subject to instability phenomena which greatly jeopardize the yields and costs of the industrial processes in which it is used.

It is the object of the present invention to overcome the drawbacks of the above technique.

In particular it has now been found, according to the present invention, that the substitution of at least one of the cysteines 243, 250 and 279 of wild type D-N-α-carbamoylase with a different amino acid residue enables this enzyme to be stabilized and improves the production yields of D-α-amino acids.

In accordance with this a first aspect of the present invention relates to mutants of D-N-α-carbamoylase with an improved enzymatic stability characterized in that at least one of the cysteines amino acid residues in position 243, 250 and 279 is substituted with a different amino acid residue selected from the group of natural amino acids.

It is another object of the present invention a nucleotidic sequence which encodes at least one mutant of D-N-α-carbamoylase with an improved stability.

The present invention also relates to a replicable expression vector comprising said sequence.

A further object of the present invention relates to a microorganism transformed with said vector.

It is another aspect of the present invention a process for the preparation of at least one mutant of D-N-α-carbamoylase with an improved stability which comprises culturing under suitable conditions a transformed microorganism and separating the mutant thus obtained.

The present invention also relates to the use of said transformed microorganisms or a mutant of D-N-α-carbamoylase obtained from said microorganism in a process for the production of D-α-amino acids.

Further objects of the present invention are evident from the text and examples which follow.

In particular, mutants of D-N-α-carbamoylase according to the present invention are characterized in that at least one of the cysteine residues (Cys) in position 243, 250 or 279 of the amino acid sequence of the wild type enzyme is substituted with a different residue selected from L-alanine, L-serine, L-lysine, L-arginine, L-aspartic acid, L-glutamic acid, L-asparagine, L-glutamine, L-histidine, L-glycine, L-leucine, L-isoleucine, L-valine, L-tyrosine, L-treonine, L-triptophane, L-phenylalanine, L-methionine or L-proline.

Mutants of D-N-α-carbamoylase of the present invention are prepared by a process which comprises:

a) introducing one or more mutations in specific sites of the gene encoding D-N-α-carbamoylase;

b) cloning the mutagenized gene obtained in step a) in a cloning vector;

c) transforming a host strain with the recombinant vector obtained in step b);

d) cultivating the host strain transformed in step c) on a suitable culture medium; and finally e) separating and purifying the mutant of D-N-α-carbamoylase thus obtained.

The introduction of a mutation in well determined sites of the gene can be carried out using one of the known mutagenesis techniques in vitro. Among the various techniques which produce modifications at a specifically defined site on a DNA sequence, the most widely-spread are those using synthetic oligonucleotides with a single strand.

In particular a modification of the method described by Zoller, M. J. and Smith, M., (1982), Nucl. Acid.Res., 10, 6487–6500) is used, which comprises:

1) inserting the gene of D-N-α-carbamoylase or part of this (target sequence) into a M13 type bacteriophage or plasmid deriving therefrom and preparing it in a single strand useful as a template for the synthesis of the mutated gene;

2) synthesizing an oligonucleotide which is complementary to the sequence to be mutagenized except for an internal portion which determines the mutation;

3) annealing the synthetic oligonucleotide to the template. This will act as primer for the synthesis of the second modified strand;

4) re-establishing, by means of a passage of polymerization and ligation in vitro, the circular structure with a double strand, of which one filament is parental, whereas the other carries the desired mutation;

5) eliminating the parental filament and re-establishing, by a passage of polymerization and ligation in vitro, the circular structure with a double strand wherein both filaments contained the desired mutation;

6) using the double strand form to transform host cells made competent by obtaining a population of mutant and wild type clones;

7) selecting the mutant clones.

With respect to the gene of D-N-α-carbamoylase to be mutagenized, this can be isolated from microorganisms such as Pseudomonas, Hansenula, Agrobacterium, Aerobacter, Aeromonas, Bacillus, Moraxella, Brevibacterium, Flavobacterium, Serratia, Micrococcus, Arthrobacter or Paracoccus. Specific examples of these microorganisms are *Bacillus macroides* ATCC 12905, *Aerobacter cloacae* IAM 1221, *Agrobacterium sp.* IP I-671, *Agrobacterium radiobacter* NRRLB 11291, *Pseudomonas sp.* FERM BP 1900.

According to a preferred embodiment of the present invention the D-N-α-carbamoylase gene derived from *Agrobacterium radiobacter* NRRLB-11291 was mutagenized.

A fragment of DNA comprising the D-N-α-carbamoylase gene was isolated from the plasmid pSM651 (CBS 203.94) by digestion with the restriction enzymes EcoRI and HindIII and, after purification by means of electrophoresis gel, it was ligated, using the known techniques, to bacteriophage M13mp8 after being digested with the same restriction enzymes. The nucleotide sequence of the coding region of the D-N-α-carbamlase gene carried by pSM651 (CBS 203.94) and the corresponding amino acid sequence are shown in the Sequence Listing as SEQ ID NO:4 and SEQ ID NO:5, respectively.

The resulting ligase mixture was used to transform cells of Escherichia coli 71/18 (E. coli) made competent as described by Dagert, M. and Ehrlich (1979), (Gene, 6: 23) and the transformants were selected on a suitable culture medium obtaining numerous positive recombinant plaques.

After preparing the single strand from one of the positive plaques, this was used as template for introducing the desired mutation. In particular the following synthetic oligonucleotides were used for introducing the Cys→Ala substitution into positions 243, 250 and 279:

(1) 5' GAG CAG CAT GGC CCC CTC CTC C 3' (SEQ ID NO:1)

(2) 5' CGC CAC GAT GGC CGA ATG GCC 3' (SEQ ID NO:2); and (3) 5' GCA GTT CCC GGG CGC GGT CGA GAT 3' (SEQ ID NO:3)

The synthesis of the oligonucleotides can be carried out with the known methods using equipment available on the market, such as for example Oligo 1000 DNA Synthesizer (Beckman).

The coupling of the single strand to the synthetic oligonucleotide which acts as primer for the synthesis of the second modified filament, is then carried out.

After obtaining the desired mutation the circular double strand structure of the target sequence, of which one filament is parental, whereas the other brings about the desired mutation, was re-established by a passage of polymerization and ligation in vitro.

The parental filament is eliminated with hexonuclease and the circular double strand structure is subsequently re-established by repolymerization and ligation. In this structure both the filaments contain the mutation.

The reaction mixture described above was used to transform competent cells of E.coli TG1, obtaining recombinant bacteriophage plaques. The carbamoylase gene contained in the genome of a positive recombinant plaque obtained from each mutagenesis experiment was sequenced using the commercial kit Sequenase® (USB) which is based on the method described by Sanger et al. (PNAS (1977), 74: 5463).

To verify the characteristics of activity and stability of the mutants of the present invention, E. coli cells transformed with a plasmid containing the gene mutagenized as described above were cultivated in a suitable medium, at 37° C. for 16 hours. The proteic extracts obtained from the cellular lysates were then analyzed by SDS-PAGE (electrophoresis on polyacrylamide gel containing sodiumdodecylsulphate) and densitometric analysis. The results showed that the mutants were expressed in quantities comparable to each other and similar to the expression level of the wild type enzyme.

The activity test carried out on the raw extracts, as described by Weatherburn, M. W., (1967), (Anal. Chem., 39: 971), showed an activity comparable to that of the wild type enzyme for all of the mutants.

Stability studies carried out at room temperature (20°–25° C.) for different times showed a higher stability than that of the wild type D-N-α-carbamoylase for the mutants tested (example 9 and FIG. 1).

In fact, whereas after 888 hours the wild type enzyme proved to have completely lost its activity, for the double mutant Cys243Ala-Cys279Ala a residuous activity of 63% was observed, which after 1896 hours was 32%.

In addition, a study carried out by putting D-N-carbamyl-parahydroxyphenylglycine in contact with the same quantities of muted enzyme Cys243Ala-Cys279Ala and wild type enzyme showed, with the same reaction time, that the mutated enzyme provides an improvement in the production yields of D-parahydroxyphenylglycine (example 10 and FIG. 2).

In accordance with the present invention the gene mutagenized as described above can be introduced into a cloning vector by correctly positioning said gene under the control of sequences which regulate its expression in the host strain.

Vectors which are suitable for the purpose can be selected from plasmids, bacteriophages and cosmids available on the market or at authorized storage centres.

Figure 1:
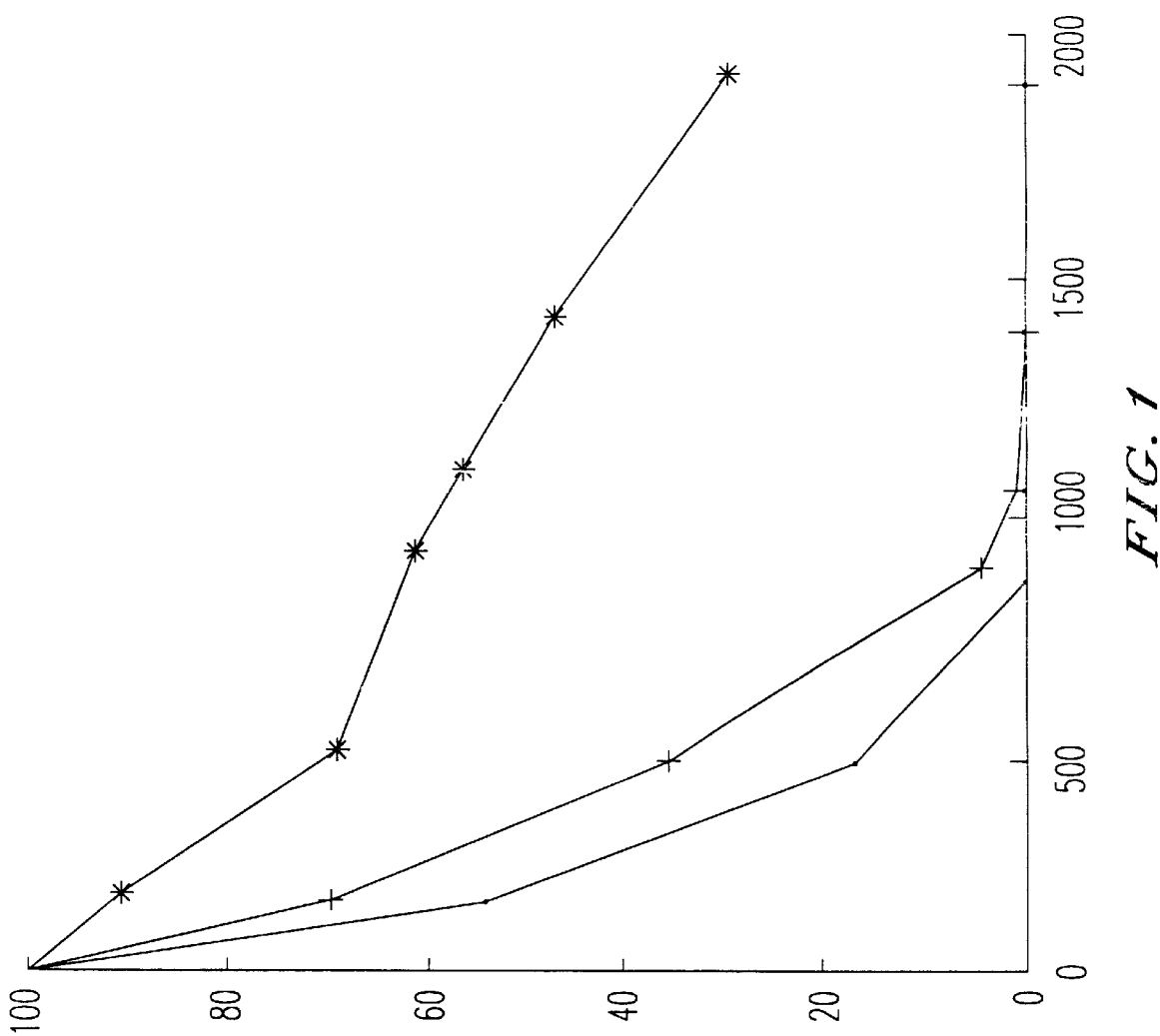
FIG. 1 shows the residual activities of the wild-type (--0--), Cys243Ala (--+--), and Cys243Ala-Cys279Ala (--*--) carbamoylases over time.

In accordance to a preferred embodiment of the present invention the mutagenized carbamoylase gene can be cloned into a plasmid containing the gene which encodes the D-hydantoinase enzyme such as for example pSM651 (CBS 203.94).

In particular this plasmid, obtained by inserting the hydantoinase and wild type carbamoylase genes (hydantoinase-carbamoylase operon) into vector pSM671 (CBS 205.94), is characterized in that it contains a synthetic promoter capable of directing with great efficiency and without inductors, the expression of the genes placed under its control in E. coli and/or B. subtilis.

The substitution of the gene encoding the wild type D-N-α-carbamoylase with the same mutagenized gene results in the construction of recombinant plasmids capable of expressing an enzymatic system, consisting of the D-hydantoinase enzyme and a mutant of D-N-α-carbamoylase.

The recombinant plasmids, containing the mutagenized D-N-α-carbamoylase gene or mutagenized hydantoinae-carbamoylase operon, can be introduced into a host microorganism selected from the B. subtilis and/or E. coli group.

These microorganisms are then cultivated under aerobic conditions, in an aqueous medium containing assimilable sources of carbon and nitrogen as well as different cations, anions and, optionaly, traces of vitamins, such as biotin or thiamine, or amino acids.

Assimilable carbon sources comprise carbohydrates such as glucose, hydrolyze amides, molasses, sucrose or other conventional carbon sources.

Examples of nitrogen sources can be selected, for example, from mineral ammonium salts, such as ammonium nitrate, ammonium sulphate, ammonium chloride or ammonium carbonate and urea or materials containing organic or inorganic nitrogen such as peptone, yeast or meat extract.

The following cations and anions are equally suitable for the purposes of the present invention: potassium, sodium, magnesium, iron, calcium, acid phosphates, sulphates, chlorides, manganese, and nitrates.

The fermentation is carried out, under stirring, at a temperature of between 25° C. and 40° C., preferably between 30° C. and 37° C. and at a pH of between 6 and 7.5, preferably between 6.5 and 7.0.

The cells (biomass), recovered from the culture medium with the conventional techniques such as centrifugation or filtration, are used in the production of D-α-amino acids or, when the cells express hydantoinase and muted carbamoylase enzymes, of racemic mixtures of 5-substituted hydantoins.

Alternatively, in the production of D-α-amino acids the cellular extract can be used, obtained from the disintegration of cells by sonication or French-Press, both purified or partially purified enzymes using the conventional techniques, or enzymes immobilized on insoluble supports.

Numerous D-N- carbamyl amino acids and hydantoins substituted in position 5 can be used in the process of the present invention. Possible substituents in position 5 are selected from a linear or branched alkyl group with a number of carbon atoms of between 1 and 6, which can be mono or polysubstituted with hydroxylic, carboxylic, sulfhydryl or aminic groups or a phenyl or benzyl group which, in turn, can contain one or more substituents in ortho, meta and para position.

Examples of 5-substituted hydantoins are: D,L-5-phenylhydantoin, D,L-5-para-hydroxyphenylhydantoin, D,L-5-methylhydantoin, D,L-5-isopropylhydantoin, D,L-5-thienylhydantoin, D,L-5-para-methoxyphenylhydantoin, D,L-5-para-chlorophenyl-hydantoin, D,L-5-benzylhydantoin.

The conversion reaction of the starting substrate (5-substituted hydantoins or D-N-carbamylamino acids) in the corresponding D-α-amino acids is preferably carried out in a nitrogen atmosphere in a hermetically closed apparatus, at a temperature of between 20° and 60° C., preferably between 30° and 45° C.

The pH of the reaction medium is maintained within values of between 6 and 10 and preferably between 7 and 8.5. This pH regulation can be carried out, for example, by adding a basic aqueous solution such as an aqueous solution of ammonia, potassium hydroxide, sodium hydroxide, sodium or potassium carbonate.

The initial concentration of the substrate is generally between 2% and 30% by weight.

The quantity of biomass or enzyme which is added to the reaction mixture depends on the particular affinity of the substrate towards the enzymes. A weight ratio biomass/substrate of between 1/1 and 1/50 can generally be used.

The D-α-amino acids prepared with the process of the present invention can be recovered from the reaction environment using the traditional methods such as ion-exchange chromatography or precipitation of the amino acid at its isoelectric point.

Although the invention relates to the production of mutants of D-N-α-carbamoylase of A. radiobacter, it is evident that it can be applied to the modification of homologous enzymes obtained from other microorganisms.

In accordance with the present invention plasmid pSM645 was deposited at the Centraalbureau Voor Schimmelcultures, SK Baarn (Holland) as E. coli SMC 306 where it was given the deposit number CBS 204.94.

The following experimental examples provide a better illustration of the present invention without limiting its scope.

EXAMPLE 1

Cloning of the Fragment EcoRI-HindIII of the Gene Encoding D-N-carbamoylase in the Replication Form of the Bacteriophage M13mp8

The plasmid pSM651 CBS 203.94 (1 μg) was digested with 1 unit of restriction enzymes EcoRI and HindIII (Boehringer) at 37° C. for 60 minutes.

After blocking the enzymatic reaction at 65° C. for 10 minutes, the reaction mixture was charged on low melting agarose gel at 0.8% and left at 50 volts for 2 hours. The EcoRI-HindIII band of 915 base pairs (bp), comprising the sequence encoding D-N-α-carbamoylase was then purified by Gelase TM (Epicentre Technologics).

The DNA fragment corresponding to this band (0.02 μg) was ligated to vector M13mp8 (50 ng) after being digested with the same restriction enzyme. The ligase reaction was carried out in 20 μl of mixture containing 66 mM Tris-HCl pH 7.6, 1 mM ATP, 10 mM $MgCl_2$, 10 mM Dithiotreitol (DTT), in the presence of 1 U of T4 DNA ligase, at 16° C. for 16 hours.

An aliquot (5 μl) of the ligase mixture was then used to transform cells of E. coli 71/18 (BRL) made competent with 50 mM of $CaCl_2$ (Dagert, M. and Ehrlich (1979), Gene, 6:23).

The transformants were subsequently selected on plates of YT agar (8 g/l Bactotryptone (DIFCO), 5 g/l NaCl) containing 40 μg/ml of X-Gal (5-bromom-4-chloro-3-indolyl-D-thiogalactopyranoside) and 125 μg/ml of IPTG (isopropyl-beta-D-thiogalactopyranoside).

Operating as specified above, numerous positive recombinant plaques (white) were obtained which could be easily distinguished from those non-recombinant (blue).

To verify if the insertion of the EcoRI-HindIII fragment had taken place correctly, the double stranded bacteriophage DNA (replication form or RF) was isolated from several positive plaques and digested with the EcoRI and HindIII enzymes (Boehringer).

The single stranded bacteriophage DNA (SS) to be used as template in the site specific mutagenesis phase was prepared from one of the positive plaques, which showed the exact insertion.

EXAMPLE 2

Site-specific Mutagenesis

The oligonucleotides used for introducing the desired mutations were synthesized with the known methods using an Oligo 1000 DNA Synthesizer (Beckman). In particular the oligonucleotides have. the following sequences:

(1) 5' GAG CAG CAT GGC CCC CTC CTC C 3' (SEQ ID NO:1) inserts mutation Cys243→Ala;

(2) 5' CGC CAC GAT GGC CGA ATG GCC 3' (SEQ ID:2) inserts mutation Cys250→Ala;

(3) 5' GCA GTT CCC GGG CGC GGT CGA GAT 3' (SEQ ID:3) inserts mutation Cys279→Ala;

The underlined bases are those used for substituting the codon of cysteine with that of alanine.

The oligonucleotides were phosphorylated at the chain-end 5' in 30 μl of reaction mixture containing 100 mM Tris-HCl pH 8, 10 mM $MgCl_2$, 5 mM DTT, 1 mM ATP and 2 U of T4 polynucleotide Kinase (Promega), by incubation at 37° C. for 30'.

The phosphorylated oligonucleotides were then used separately in three mutagenesis reactions in vitro using the system "Oligonucleotide—directed in vitro mutagenesis version 2" (Amersham), based on the method described by Zoller and Smith (1983, Methods in Enzymol., 100: 468–500), operating according to the indications of the producer.

The reaction mixtures were then used to infect cells of E. coli TG1 (Amersham) as specified above.

The bacteriophage DNA deriving from a white plaque obtained from each mutagenesis experiment was sequenced by means of the "Sequenase 2.0" kit (United States Biochemical) based on the method described by Sanger et al. (PNAS (1977) 74: 5463) to verify the presence of the desired mutation.

EXAMPLE 3

Subcloning of the Mutants Cys→Ala in the Plasmid pSM671

1.0 μg of each of the double stranded DNAs of the recombinant bacteriophages containing the substitution of cysteine with alanine was digested with the restriction enzymes EcoRi and HindIII (2 U) and, subsequently ligated with the plasmid pSM671 CBS 205.94 (1 μg) previously cut with the same restriction enzymes. The ligase reaction was carried out in 20 μl of ligase buffer containing 2 U T4 DNA ligase, 150 ng of bacteriophage DNA and 50 ng of plasmid DNA, at 16° C. for 16 hours.

5 μl of each mixture were then used to transform ompetent cells of E. coli 71/18 (BRL).

The transformants were selected on plates of LB agar medium (0.8% Bacto triptone, 0.5% Yeast extract, 0.5% NaCl, agar 18 g/l) containing μg/ml of chloramphenicol.

The plasmid DNA isolated from one of the positive Cm$^r$ clones (chloramphenicol resistent) thus obtained, was analyzed by means of restriction analysis to verify the correct insertion of the gene.

The plasmids thus obtained were called pSM641 (carrying mutation Cys243→Ala), pSM642 (carrying mutation Cys250→Ala), pSM643 (carrying mutation Cys279→Ala).

EXAMPLE 4

Expression of the Mutants in E. coli

The E. coli strains carrying plasmids pSM641, pSM642 and pSM643, were inoculated into 50 ml flasks each containing 10 ml of LB medium to which 20 μg/ml of chloramphenicol had been added and incubated at 37° C. for 16 hours, under stirring (200 rpm). As a control, the strain of E. coli 71/18 containing plasmid pSM637 carrying the wild type gene of carbamoylase was cultured under the same conditions described above.

The cultures were then centrifuged at 12,000 rpm for 1 minute (rotor SJ14, Beckman). The cells thus obtained were resuspended in 300 μl of buffer 20 mM Tris-HCl pH 7.5, 20 mM BMeOH, 20% glycerol and lysed by sonication (Soniprep150, MSE 1 minute impulses, at average voltage). 20 μl of each lysate were analyzed by SDS-PAGE and activity test.

The electrophoretic analysis showed that all the enzymes were expressed in a comparable quantity among each other and to the expression level of the wild type enzyme.

EXAMPLE 5

Construction of the Double Cys→Ala Mutants

Using the site-specific mutagenesis process described in example 2, mutants were obtained containing the double mutations Cys243Ala-Cys250Ala and Cys243Ala-Cys279Ala. The only expedient was to prepare two reaction mixtures in which two oligonucleotides containing the mutations to be introduced (respectively oligonucleotides 1 and 2 for mutant Cys243Ala-Cys250Ala and oligonucleotides 1 and 3 for mutant Cys243Ala-Cys279Ala), had been added contemporaneously. After the in vitro mutagenesis reaction, each mixture was used to transform cells of E. coli TG1. The plasmid DNA isolated from one of the white plaques obtained from each transformation was sequenced to verify the correct substitution of the cysteines. The recombinant bacteriophages selected were then used for the preparation of the double stranded DNA.

EXAMPLE 6

Subcloning of the Double Mutants in the Plasmid pSM671

Using the same procedure as described in example 3, the carbamoylase genes containing the two mutations were subcloned from the bacteriophage DNA in plasmid pSM671 CBS 205.94. Analysis of the resulting plasmids showed the correct insertion of the carbamoylase gene. The plasmids obtained were called pSM644 (carrying the double mutation Cys243Ala-Cys250Ala) and pSM645 (carrying the double mutation Cys243Ala-Cys279Ala).

The clone of E. coli comprising plasmid pSM645 was indicated with the abbreviation SMC306.

EXAMPLE 7

Expression of the Double Mutants in E. coli

Cells of E. coli containing plasmids pSM644 and pSM645 were cultivated under the same conditions described in example 4. Electrophoretic analysis of the cellular lysates showed that the mutated enzymes were expressed at levels comparable to those of the wild type enzyme.

EXAMPLE 8

Purification of the Mutants

The biomasses coming from the fermentations of strains of E. coli containing respectively plasmids pSM641, pSM645 and pSM637 (control) were suspended in buffer Tris-HCl 25 mM, pH 7.0, glycerol 20% (v/v) (Buffer A) and lysed by two passages in the French Press at 18,000 psi.

The supernatants obtained after centrifugation of the lysates (30,000 rpm, 4° C., 30 minutes) were charged onto a Sepharose® Q FF (Pharmacia) column (2.6×20 cm) balanced with buffer A. The column was subsequently washed with buffer A (3 volumes of column) and then eluated with a gradient of NaCl of between 0 and 0.4M. The fractions containing the enzymatic activity were collected and charged onto a Fast Flow Chelating Spharose® (Pharmacia). column (2.6×20 cm) activated with nickel chloride and balanced with buffer A.

After washing the column with buffer A, it was eluted with a gradient of imidazol of between 0 and 0.2M in the same buffer. The fractions containing the enzymatic activity were collected and concentrated by ultrafiltration on a YM10 membrane (Amicon). The concentrated solutions were then charged onto a Superose® 12 HR 10/30 (Pharmacia) column balanced with buffer A and eluated with the same buffer. The fractions containing the enzymatic activity, analyzed on SDS-PAGE at 12.5% revealed the presence of a protein with a molecular weight equal to about 36,000 daltons, with a purity higher than 90%.

The specific activities of the purified proteins measured using as substrate D-carbamylparahydroxyphenylglycine 0.12M in buffer NaPO$_4$ 0.2M pH7.0 resulted comparable to each other and were between 8 and 9 U/mg, a similar value to that of the wild type enzyme.

The term units refers to the quantity of enzyme capable of transforming 1 pmole of substrate in 1 minute at 40° C.

EXAMPLE 9

Analysis of the Enzymatic Stability of the Mutants

The enzymatic solutions obtained as described in example 8, were filtered under conditions of sterility on DynaGard of 0.2 μm (Microgon, Inc.). Aliquots (0.2 ml) of said filtrates were then introduced in Eppendorf sterile test-tubes and maintained at room temperature (20°–25° C.). At regular intervals of time the residual enzymatic activity was determined at 40° C. dosing the D-para-hyroxyphenylglycine formed via HPLC using as substrate D-N-carbamylparahydroxyphenylglycine in a buffer of sodium phosphate 0.2M, pH 7.0.

Table 1 and FIG. 1 show in percentages the residual activities (ordinate) of the wild type carbamoylase (—o—) and mutants Cys243Ala (—+—) and Cys243Ala-Cys279Ala (—*—) with respect to the time expressed in hours (abscissa).

TABLE 1

| | RESIDUAL ENZYMATIC ACTIVITY (%) | | |
|---|---|---|---|
| Time (h) | WT | Cys243Ala | Cys243Ala–Cys279Ala |
| 0 | 100 | 100 | 100 |
| 168 | 55 | 70 | 91 |
| 480 | 18 | 36 | 70 |
| 888 | 0 | 5 | 63 |
| 1056 | 0 | 1 | 58 |
| 1896 | 0 | 0 | 32 |

EXAMPLE 10

Figure 2:
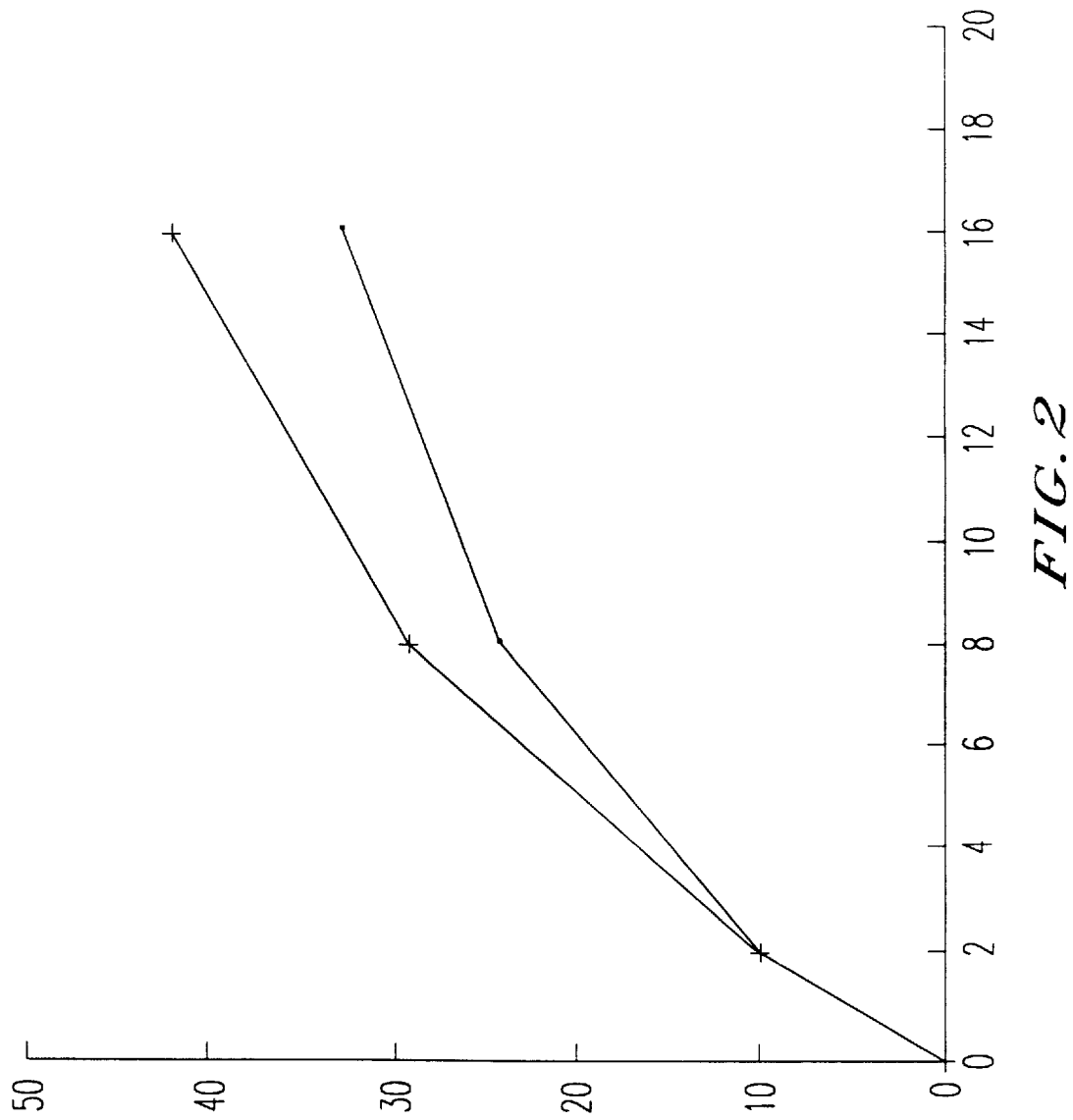
FIG. 2 shows the production of D-parahydroxyphenylglycine produced by wild-type (-- --) and mutant (--+--) carbamoylases over time.

Comparison Between the Productivity of Wild Type Carbamoylase and Mutant Cys243Ala-Cys279Ala The same quantities (0.064 units/ml) of wild type carbamoylase and mutated carbamoylase Cys243Ala-Cys279Ala were introduced into two devices thermostat-regulated at 40° C., containing D-N-carbamyl parahydroxyphenylglycine (25.2 mg/ml) in 100 ml of buffer Na-phosphate 0.2M pH 7.0. At regular intervals of time the quantity of D-parahydroxyphenylglycine produced was determined via HPLC. The results obtained are shown in FIG. 2, where in abscissa there is the time in hours and in ordinate the quantity of amino acid expressed as μMoles/ml; with — — wild type carbamoylase and (—+—) mutant of carbamoylase.

---

What is claimed is:

1. Stable mutants of D-N-α-carbamoylase which have at least one of the Cysteine amino acid residues in positions 243, 250 and 279 of the amino acid sequence of wild type D-N-α-carbamoylase substituted with a different amino acid residue selected from the group consisting of L-Alanine, L-Arginine, L-Asparagine, L-Aspartic acid, L-Cysteine, L-Glutamine, L-Glutamic acid, L-Glycine, L-Histidine, L-Isoleucine. L-Leucine, L-Lysine, L-Methionine, L-Phenylalanine, L-Proline, L-Serine, L-Threonine, L-Tryptophan, L-Tyrosine, and L-Valine.

2. The mutant of claim 1, wherein the natural amino acid residue is L-alanine.

3. The mutant of claim 1, wherein both the cysteine amino acid residues in positions 243 and 279 are substituted with L-alanine residue.

4. A process for the production of D-α-amino acids, comprising:
stereospecifically converting D-N-carbamoyl amino acids or racemic mixtures of 5-substituted hydantoins in the presence of a mutant of D-N-α-carbamoylase and/or an enzymatic system consisting of D-hydantoinase and the mutant of D-N-α-carbamoylase, wherein the mutant of D-N-α-carbamoylase has at least one of the Cysteine amino acid residues in positions 243, 250 and 279 of the amino acid sequence of wild type D-N-α-carbamoylase substituted with a different amino acid residue selected from the group consisting of L-Alanine, L-Arginine, L-Asparagine, L-Aspartic acid, L-eyst-ene, L-Glutamine, L-Glutamic acid, L-Glycine, L-Histidine, L-Isoleucine, L-Leucine, L-Lysine, L-Methionine, L-Phenylalanine, L-Proline, L-Serine, L-Threonine, L-Tryptophan, L-Tyrosine, and L-Valine and isolating the D-α-amino acids therefrom.

5. The process of claim 4, wherein the conversion reaction is conducted in the presence of a mutant of D-N-α-carbamoylase and/or an enzymatic system consisting of D-hydantoinase and a mutant of D-N-α-carbamoylase isolated from a microorganism capable of producing said mutant and/or said enzymatic system.

6. The process of claim 5, wherein a mutant of D-N-α-carbamoylase and/or the enzymatic system comprising said mutant are immobilized on an insoluble solid support.

* * * * *